(12) United States Patent
Esenaliev et al.

(10) Patent No.: US 6,751,490 B2
(45) Date of Patent: Jun. 15, 2004

(54) CONTINUOUS OPTOACOUSTIC MONITORING OF HEMOGLOBIN CONCENTRATION AND HEMATOCRIT

(75) Inventors: Rinat Esenaliev, Galveston, TX (US); Massoud Motamedi, Houston, TX (US); Donald Prough, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 338 days.

(21) Appl. No.: 09/796,992

(22) Filed: Mar. 1, 2001

(65) Prior Publication Data

US 2004/0054268 A1 Mar. 18, 2004

Related U.S. Application Data

(60) Provisional application No. 60/186,193, filed on Mar. 1, 2000.

(51) Int. Cl.$^7$ ................................................. A61B 5/00
(52) U.S. Cl. ........................... 600/310; 600/322; 606/2
(58) Field of Search ................................. 600/310, 316, 600/322, 331, 336, 473, 476, 323, 328; 250/252.1; 606/2, 7, 10, 12, 15, 17–18

(56) References Cited

U.S. PATENT DOCUMENTS

| 4,028,933 | A |   | 6/1977  | Lemons et al. ............... 73/67.6 |
|-----------|---|---|---------|--------------------------------------|
| 4,212,206 | A |   | 7/1980  | Hartemann et al. ........... 73/606   |
| 4,430,897 | A |   | 2/1984  | Quate .......................... 73/606 |
| 4,710,030 | A |   | 12/1987 | Tauc et al. ................... 356/432 |
| 4,727,420 | A |   | 2/1988  | Kohda et al. ................ 358/112  |
| 4,953,539 | A | * | 9/1990  | Nakamura et al. ........... 600/109   |
| 5,041,121 | A |   | 8/1991  | Wondrazek et al. ......... 606/128    |
| 5,136,172 | A |   | 8/1992  | Nakata et al. ............... 250/572  |
| 5,141,331 | A |   | 8/1992  | Oehler et al. ................ 374/118 |
| 5,178,836 | A |   | 1/1993  | Kitamori et al. ............... 422/73 |
| 5,254,112 | A |   | 10/1993 | Sinofsky et al. ................ 606/7 |
| 5,293,873 | A |   | 3/1994  | Fang ........................... 128/664 |
| 5,348,002 | A | * | 9/1994  | Caro                                  |
| 5,348,003 | A | * | 9/1994  | Caro ........................... 600/310 |
| 5,349,954 | A | * | 9/1994  | Tiemann et al. ............. 600/342   |
| 5,398,685 | A |   | 3/1995  | Wilk et al. ................ 128/653.1 |
| 5,421,337 | A |   | 6/1995  | Richard-Kortum et al. . 128/665      |
| 5,465,722 | A |   | 11/1995 | Fort et al. ............... 128/661.01 |
| 5,582,578 | A |   | 12/1996 | Zhong et al. .................. 601/4  |
| 5,583,634 | A |   | 12/1996 | Andre et al. ................. 356/318 |
| 5,596,986 | A | * | 1/1997  | Goldfarb .................... 600/323  |
| 5,602,894 | A |   | 2/1997  | Bardash ....................... 378/87  |
| 5,615,675 | A |   | 4/1997  | O'Donnell et al. ....... 128/653.1    |

(List continued on next page.)

FOREIGN PATENT DOCUMENTS

| DE | 4400674 A1    | 7/1995 | .......... G01N/21/31 |
|----|---------------|--------|----------------------|
| EP | 0 282 234 A1  | 9/1988 | ............ A61B/5/00 |
| EP | 0 919 180 A1  | 2/1999 | ............ A61B/5/00 |
| EP | 919 180 A1    | 6/1999 | ............ A61B/5/00 |
| WO | WO 01/10295 A1| 2/2001 | ............ A61B/5/00 |

OTHER PUBLICATIONS

PCT International Search Report. PCT/US 02/23620.
Anesthesia & Analgesia 2001; 92; s1–s363. "Continuous Noninvase Optoacoustic Monitoring of Hemoglobin Saturation". Deya, Esenaliev, et. al.
The PCT International Search Report.

*Primary Examiner*—Tu Ba Hoang
(74) *Attorney, Agent, or Firm*—Robert W. Strozier

(57) ABSTRACT

An optoacoustic apparatus is disclosed which includes a radiation source of pulsed optical radiation and a probe having a front face to be placed in contact with a tissue site of an animal body. The probe further includes an optical fiber terminating at the surface of the front face of the probe and connected to a pulsed laser. The front face of the probe also has mounted therein or thereon a piezoelectric transducer for detecting an acoustic response to the radiation pulses connected to a processing unit which converts the transducer signal into a measure of hemoglobin concentration and/or hematocrit of blood.

25 Claims, 11 Drawing Sheets

U.S. PATENT DOCUMENTS

| | | | |
|---|---|---|---|
| 5,840,023 A | 11/1998 | Oraevsky et al. | 600/407 |
| 5,977,538 A * | 11/1999 | Unger et al. | |
| 6,049,728 A | 4/2000 | Chou | 600/316 |
| 6,064,898 A * | 5/2000 | Aldrich | 600/316 |
| 6,125,290 A * | 9/2000 | Miesel | 600/325 |
| 6,175,759 B1 * | 1/2001 | Chan et al. | 600/431 |
| 6,309,352 B1 | 10/2001 | Oraevsky et al. | 600/407 |

* cited by examiner

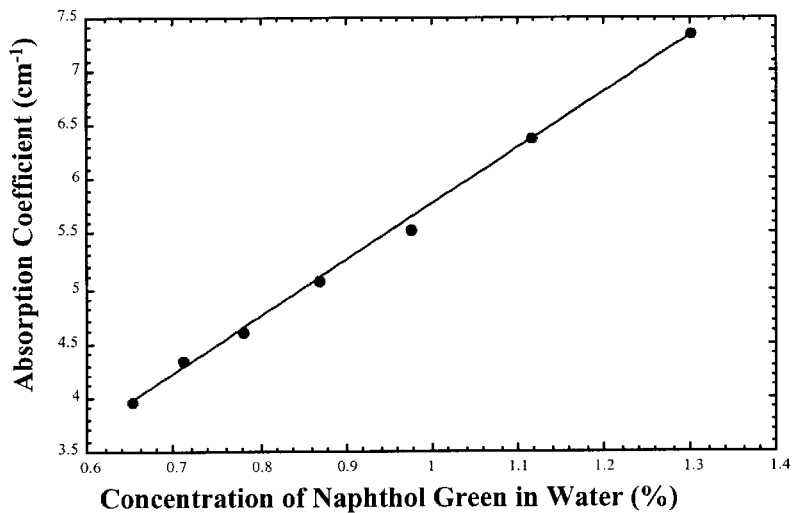
FIG. 9
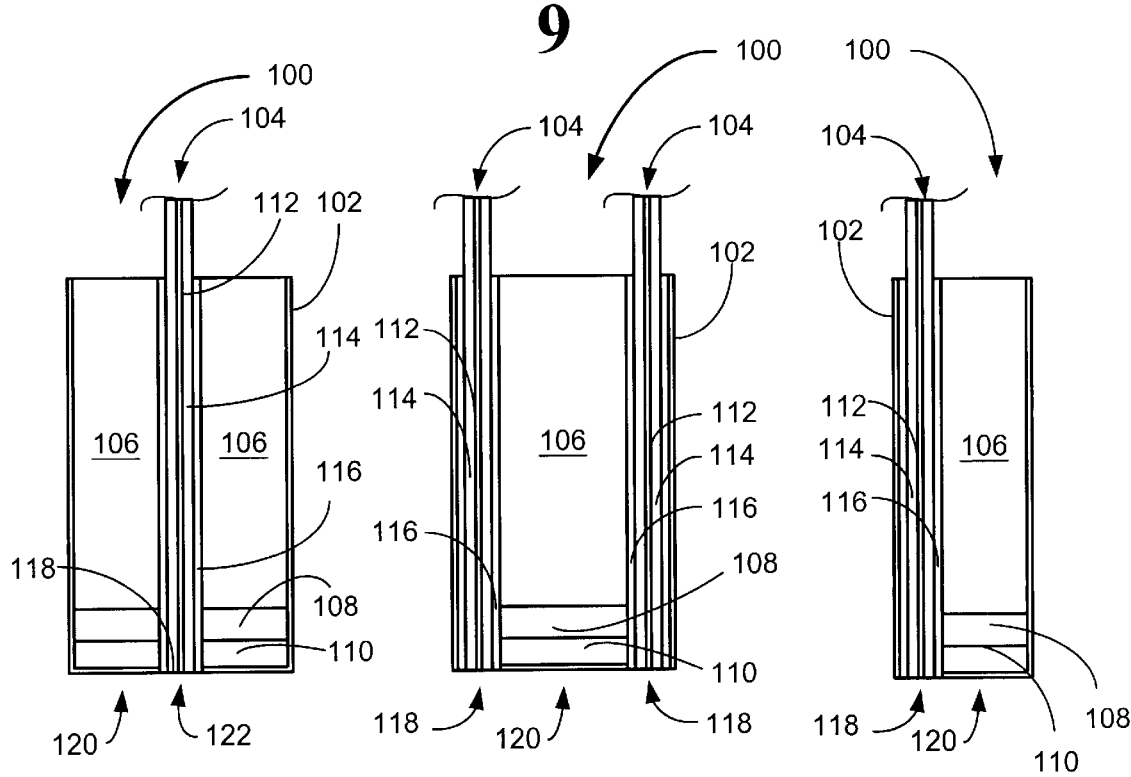
FIG. 10A  FIG. 10B  FIG. 10C

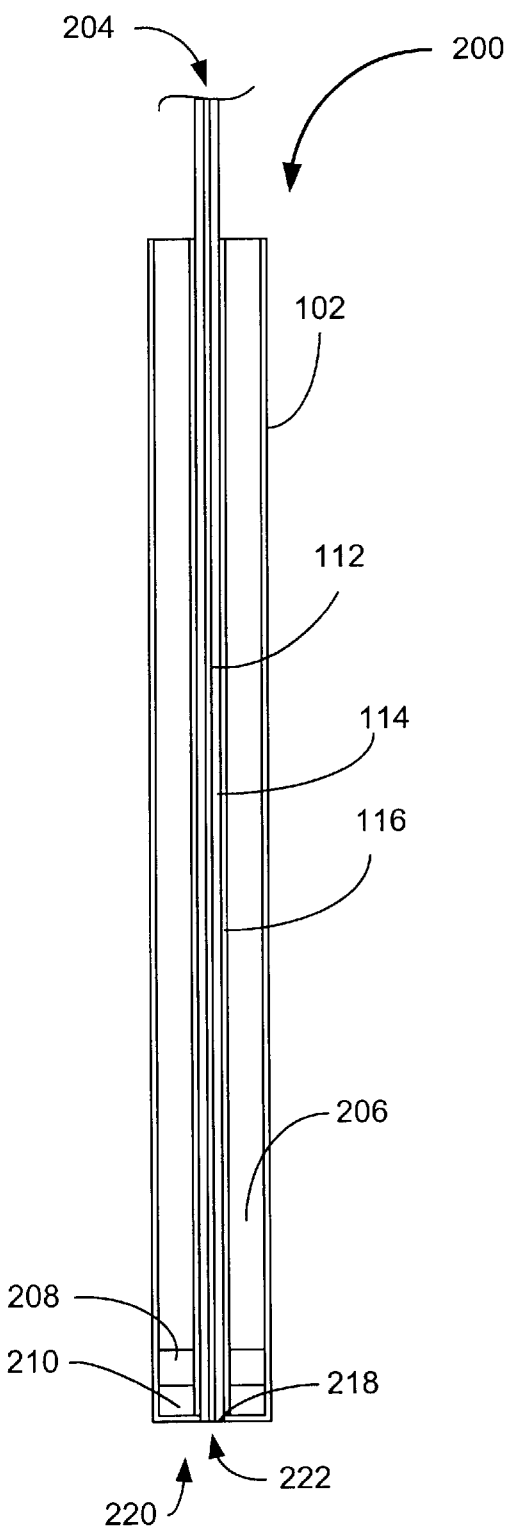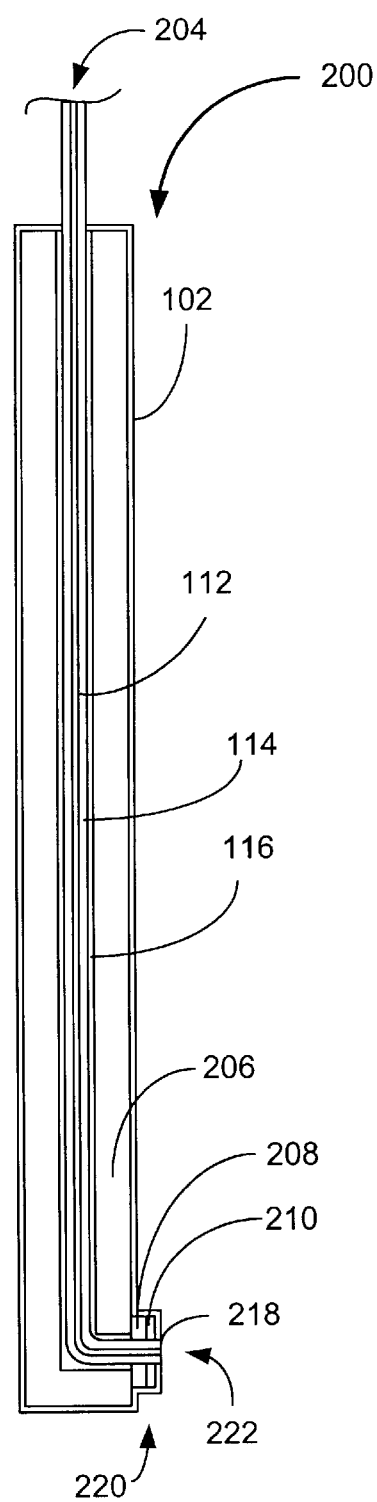
FIG. 10D  FIG. 10E

CONTINUOUS OPTOACOUSTIC MONITORING OF HEMOGLOBIN CONCENTRATION AND HEMATOCRIT

RELATED APPLICATIONS

This application claims provisional priority to U.S. Provisional Patent Application Serial No. 60/186,193 filed Mar. 1, 2000, incorporated herein by reference.

BACKGROUND OF THE INVENTION

1. Field of the Invention

The present invention relates to an apparatus for non-invasive, real-time, accurate, continuous monitoring of hemoglobin concentration and hematocrit and a method for continuously or discretely monitoring hemoglobin concentration and hematocrit.

More particularly, the present invention relates to an optoacoustic apparatus including a nanosecond pulsed-laser, a fiber-optic delivery system and a probe including a sensitive acoustic transducer and hardware and software for converting a received acoustic signal into a measurement of hemoglobin concentration and hematocrit and to methods for monitoring hemoglobin concentration and hematocrit using the apparatus and methods for making the apparatus.

2. Description of the Related Art

Continuous noninvasive monitoring of blood hemoglobin concentration and hematocrit offers great promise in the diagnosis and management of many diseases and life-threatening conditions, such as emergency department stabilization of hemorrhaging patients, management of critically ill patients in Intensive Care Units, and performance of extensive surgical procedures. Current techniques are invasive, requiring blood sampling and analysis, and cannot be performed continuously, in real time for extended intervals. Presently, there is no system for accurate, non-invasive, and continuous monitoring of hemoglobin concentration and hematocrit.

Because of the importance of hemoglobin concentration in oxygen delivery, hematocrit and hemoglobin are among the most frequently obtained blood tests in both outpatients and inpatients. Current techniques for measuring hemoglobin concentration and hematocrit require withdrawal of a blood sample from a vein or artery. Subsequently, the sample can be centrifuged, separating the fraction of red cells from plasma or chemically analyzed. These techniques are accurate but invasive and can result in iatrogenic anemia in patients who require frequent blood sampling [3–7]. Continuous invasive techniques are available for monitoring hemoglobin concentration, but these require access to an extracorporeal loop containing circulating blood (as is present, for example, during hemodialysis) [8–12]. Although noninvasive techniques such as pulse oximetry are available to monitor arterial oxygen saturation, no noninvasive technique is available to monitor hemoglobin concentration or hematocrit.

One additional major problem with intermittent measurement of hemoglobin concentration or hematocrit is the inevitable delay associated with withdrawal of a blood sample, transport to a measuring device, and processing. If the laboratory is remote from the site of care, the delay can be considerable. Even if the laboratory is in close proximity to the site of care, frequent sampling in a critically ill patient may occupy a substantial proportion of a technician's time, thereby increasing the cost of care and limiting the availability of that technician for other duties.

Thus, there is a need in the art for a non-invasive, real-time, accurate, continuous apparatus and a method using the apparatus for monitoring hemoglobin concentration and hematocrit.

SUMMARY OF THE INVENTION

The present invention provides an optoacoustic apparatus including a nanosecond pulsed laser and a fiber-optic delivery system including a plurality of optical fibers, where the system is connected to an output of the laser at its proximal end. The apparatus also includes a probe including a piezo-electric transducer mounted in a front face of the probe and a back portion adapted to receive the fiber-optic delivery system. The optical fibers terminate at the front face of the probe and are distributed around or surround the transducer. The transducer is connected via a cable which exits out of the back of the probe to a processing unit that converts the transducer output into a continuous measure of hemoglobin concentration and hematocrit.

The present invention also provides an optoacoustic apparatus for monitoring hemoglobin concentration in the aorta of an animal comprising a pulsed radiation source; an optical system including an optical fiber, an optical screen and an acoustic screen, where the system is connected to an output of the radiation source at its proximal end; a probe including a housing, a tip, a ring-shaped piezoelectric element, a backing element and an isolating layer, where the optical system enters the housing at its proximal end passes through a center of the piezoelectric element and terminates flush with the housing at the probers tip; a cable connected to the transducer at its proximal end and exiting the probe out of the proximal end of the probe; and a processing unit connected to the distal end of the cable for converting the transducer output into a measure of aorta hemoglobin concentration and/or hematocrit.

The present invention also provides a probe including a front face having mounted thereon a piezoelectric transducer connected to an output cable that exits a back portion of the probe, a plurality of optical fibers entering the probe from the back portion of the probe and terminating at or in the front face of the probe, where light from a laser is sent through the fibers and exit the probe at its front face causing an acoustic response which is measured by the transducer mount in the probe.

The present invention further provides a method for continuously measuring optoacoustic monitoring of hemoglobin concentration and hematocrit including the step of directing radiation pulse from a laser via optical fibers into a probe of present invention having its front face in contact with a tissue site (blood vessel) of an animal including human. The light pulse leaves the probe face and enters the tissue site causing the production of an acoustic signal. The acoustic signal is received by a transducer mounted on the front face of the probe. The signal is then transmitted to a processing unit which converts the signal into a measure of hemoglobin concentration and hematocrit. The method can also include displaying the measurement on a display device. Preferably, the radiation is pulsed and particularly, the radiation is pulsed in a nanosecond time frame.

The present invention also provides a system for carrying out the above-stated method including a pulsed laser system or other system capable of generating short optical pulses to provide irradiation of a tissue or vessel. The systems also includes a light communication system such as a fiber-optic system or articulated mirror arm optical system for delivering laser pulses to the tissue or vessel and an acoustic detection systems including at least one acoustic transducer for pressure profile detection with sufficient sensitivity, temporal resolution, and bandwidth so that thermoelastic optoacoustic pressure profiles of the absorbed laser energy in the tissue or vessel can be detected. The system also includes an adjustable holder for the light delivery system and the acoustic transducer(s) to provide appropriate irradiation conditions and acoustic contact between the investigated tissue or vessel and the acoustic transducer(s) and an electronic system for signal recording and processing. The system can also include a digital processing or computer system that converts a signal from the acoustic detection system into a measure the hemoglobin concentration of blood in a tissue or vessel.

The present invention still further provides a method for relating an acoustic signal to an hemoglobin concentration of arterial or venous blood in a tissue site of an animal including a human.

DESCRIPTION OF THE DRAWINGS

The invention can be better understood with reference to the following detailed description together with the appended illustrative drawings in which like elements are numbered the same:

FIG. 9 depicts a graph of absorption coefficient of naphthol green solution calculated from the optoacoustic slopes as a function of concentration. The solution was irradiated through 1-cm turbid gelatin slab;

FIGS. 10A–C depict three preferred embodiment of an optoacoustic probe of this invention;

FIGS. 10D–E depict two preferred embodiment of an optoacoustic probe of this invention for use in the esophagus for monitoring hemoglobin concentration in aorta blood;

DETAILED DESCRIPTION OF THE INVENTION

Figure 1:
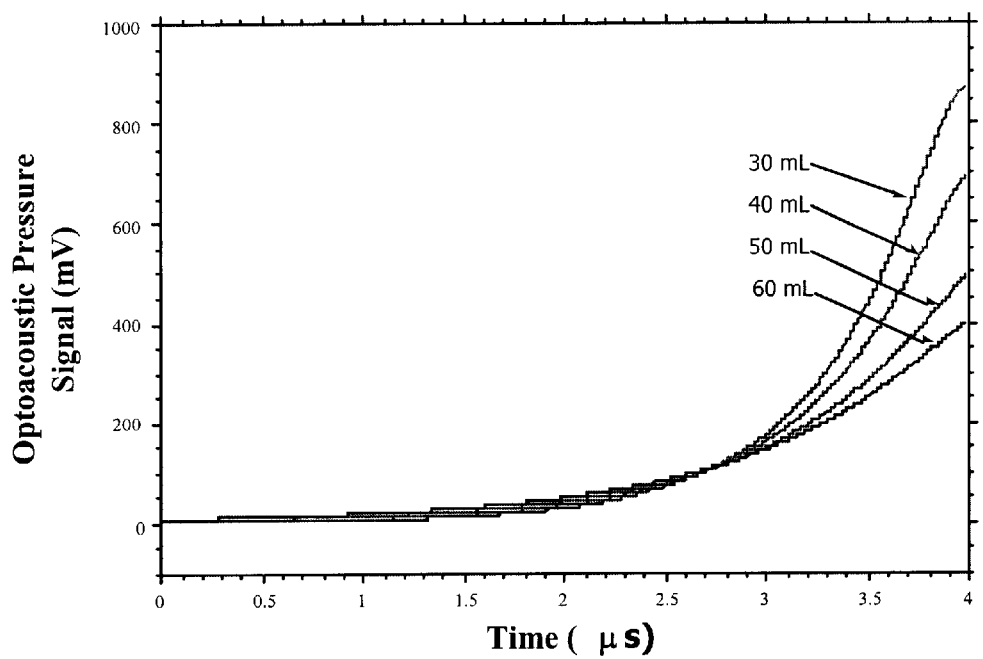
FIG. 1 depicts a graph of optoacoustic signals induced in blood at different volumes.

The inventors have found that a new and efficient monitor can be constructed for monitoring hemoglobin concentration and hematocrit using an optoacoustic monitoring apparatus. The inventors have also found that a method using the optoacoustic monitoring apparatus can be implemented manually or automatically (computer) controlled and supervised for monitoring on a continuous or discrete basis hemoglobin concentration and hematocrit. The present invention can be used in animals, where an animal is any member of the animal kingdom, including, without limitation, mammals and especially humans.

The inventors have found a novel technique that accurately monitors and quantifies blood hemoglobin concentration and hematocrit. This technique is based on generation of ultrasonic (optoacoustic) waves in blood circulating in vessels via short optical pulses and detection of these waves by a sensitive acoustic transducer. The temporal characteristics and amplitude of these waves are dependent on hemoglobin concentration and hematocrit. Since the optoacoustic waves can propagate in tissues with low attenuation and distortion, this technique has high resolution and permits localization of vessels of interest with high accuracy. This localization permits direct detection and measurement of signals induced in blood circulating in vessels without signal contamination from tissues between the transducer and blood. The present invention is ideally-suited for non-invasive, continuous monitoring of hemoglobin concentration in blood by measuring induced acoustic signals in tissues and vessels such as the aorta, radial, femoral, carotid arteries or other blood vessels.

The present invention relates to a method of hemoglobin concentration monitoring that comprises the steps of: irradiating a blood vessel with at least one optical pulse resulting in an optoacoustic pressure wave in the vessel; time-resolved detecting of the optoacoustic wave with an acoustic detector; analyzing a temporal profile and/or amplitude of the optoacoustic wave with a processing unit including computer software adapted to convert the wave data into digital data; and calculating a hemoglobin concentration in blood in the vessel.

The present invention relates to a system for carrying out the method of this invention including a pulsed laser system or other generator of short optical pulses to provide irradiation of a vessel or tissue site; a fiber-optics system or an articulated mirror arm optical system for delivery of the radiation pulses to the vessel or site; an acoustic transducer for pressure wave detection with sufficient sensitivity, temporal resolution, and bandwidth to detect the pressure wave; an adjustable holder for the light delivery system and the acoustic transducer to provide appropriate irradiation conditions and acoustic contact between the vessel or tissue and the acoustic transducer; an electronic system for signal recording and processing; a computer or digital processing unit for converting the pressure wave detected by the transducer into a hemoglobin concentration based on an analysis of the recorded optoacoustic pressure wave profile and amplitude. Preferably, the radiation source emits light in the spectral range from about 400 to about 2500 nm. The apparatus can include one or more radiation sources as described in U.S. Pat. No. 5,840,023 and co-pending application Ser. Nos. 09/179,791 and 09/633,597. Although the optical and transducer part of the probe can be housed in separate probes, it is preferably to have the optical and acoustic part of the apparatus in the same probe.

One preferred application of this invention is to measure a hemoglobin concentration in blood in the aorta or other artery that is not skin accessible. Another preferred application of this invention is to measure hemoglobin concentration in arteries that can be measure by situating the probe on the skin of the patient near the artery such as a radial artery, a carotid artery, a brachial artery, femoral artery or other artery.

The method of this invention can be applied to any vessel including arteries or veins. The veins can be under the skin or in a hollow organ. For veins the radiation is preferably of wavelengths of about 548, 568, 587, and 805 nm or the isobestic points and in the spectral ranges from about 400 to about 640 and above 1120 nm where absorption coefficients of oxy- and deoxygenated blood are close to each other.

The preferred radiation sources include light derived from the first harmonic (1064 nm) or the second harmonic (532 nm) of Nd:YAG laser or tunable lasers such as a Ti:Sapphire laser or a dye laser or an optical parametric generators or mixtures or combinations thereof.

The present invention also relates to a method wherein the above recited method is used for hematocrit measurements in the spectral range from 400 to 2500 nm and preferably in the spectral range above 1350 nm where optoacoustic signal characteristics are more sensitive to the changes in blood scattering and, therefore, to changes in hematocrit. The method can be used for blood volume measurements, for ultrasound-guided optoacoustic monitoring of fetal anemia during pregnancy, for measurements of hematocrit and hemoglobin in cord blood, for hemoglobin concentration monitoring in patients with kidney failure and dialysis.

The probe for use in this invention will generally include between 1 and 144 optical fibers, preferably, between about 6 to about 60 optical fibers, particularly, between about 12 and about 48 and especially between about 18 and 36, with 24 optical fibers being most preferred for probes designed to contact the skin. For probes designed to contact the wall of the esophagus so the Hb concentration in the aorta can be monitored, such probes will include between 1 and about 20 optical fibers, with between about 1 and about 10 being preferred, and between about 1 and about 5 being particularly preferred. The optical fibers have diameters between about 10 $\mu$m to about 5 mm, preferably, between about 0.1 mm and 2 mm, particularly between about 0.2 mm and 1.5 mm. For esophagus probes (needle probes), the smaller diameter fiber are preferred. These needle probes can also be used to monitor Hb concentration in various regions of the heart during bypass surgery or other myocardial surgical procedures.

The probes also include a sensitive acoustic transducer having a size controlled by the application and by design criteria. The optical fiber and transducer are preferably contained in a single housing to provide stable irradiation and detection conditions. For skin applications, the fibers can be mounted around the transducer, adjacent to the transducer or in the center of a ring shaped transducer. For aorta monitor via the esophagus wall, the fiber(s) can mounted within a center of a ring shaped piezoelectric element, surrounding a disk shaped transducer or adjacent to the transducer.

A sensitive wide-band transducer is designed to detect optoacoustic waves from blood circulating in a target vessel or tissue such as the aorta or other blood vessels. The choice of optimal designs of and materials for the piezoelectric element and the acoustic transducer depend on a number of parameters: bandwidth, sensitivity, acoustic impedance matching to tissues, etc. For example, polyvinylidene fluoride (PVDF) slabs are suitable transducers for sensitive detection of optoacoustic waves from vessels and/or tissues. The inventors have found that a PVDF slab having a thickness between about 10 $\mu$m to about 1 mm thick is preferred. Other suitable piezoelectric materials include, without limitation, PZT, lithium niobide or other similar piezoelectric materials. The present invention can also use other pressure sensing devices such as optical devices that measure the acoustic waves optically such as interferometric devices or other similar devices.

Importance and Significance

In this invention the inventors disclose a novel technique for noninvasive continuous monitoring of hemoglobin concentration and hematocrit in blood. The monitor can be used for (1) noninvasive measurement of hemoglobin concentration without blood sampling and standard blood testing and (2) continuous measurement of hemoglobin concentrations during surgical procedures, saline or drug infusions, blood infusions, and infusions of stroma-free hemoglobin.

The apparatuses and methods of this invention are ideally-suited for monitoring hemoglobin concentration in several large patient populations, including, without limitation, normal subjects, patients with blood diseases, and patients with a variety of other conditions. For example, patients who suffer hemorrhage secondary to multisystem trauma being treated in an emergency department, typically have a nearly normal hemoglobin concentration because both blood and plasma have been lost. However, as resuscitation begins with red cell-free fluids, the patient's hemoglobin concentration can and often does decrease rapidly.

A continuous measurement of hemoglobin concentration would permit prompt recognition of the need to include red cell containing fluids during resuscitation and would also provide early evidence of continued hemorrhaging. Patients in Intensive Care Units often suffer from blood loss through gastrointestinal hemorrhage and blood loss from other sites, including blood sampling for diagnostic purposes.

A continuous, noninvasive measurement of hemoglobin concentration would permit prompt diagnostic and therapeutic interventions and would also reduce iatrogenic blood loss necessitated by the need to obtain blood samples for current hemoglobin measurements. During major surgery, particularly surgery involving major blood vessels, the availability of a continuous measurement of hemoglobin concentration would permit not only prompt administration of needed red cells, but also would facilitate avoidance of unnecessary transfusion by demonstrating that hemoglobin exceeded an acceptable concentration.

Maintenance of adequate systemic oxygen delivery (cardiac output multiplied by arterial oxygen content) is one of the principal clinical goals in caring for acutely traumatized patients, patients undergoing intensive care, and patients undergoing extensive surgery. However, many chronic diseases, such as chronic renal failure, also are associated with anemia and require intermittent measurement of hemoglobin concentration or hematocrit. Because virtually all blood oxygen content consists of oxygen combined with hemoglobin, oxygen content bears a linear relation to hemoglobin concentration and reduction of hemoglobin concentration requires physiologic compensation, such as increased cardiac output.

Although the normal hemoglobin concentration is between about 13 and about 15 grams/dL, otherwise healthy individuals tolerate reductions of hemoglobin to levels as low as 7 g/dL or less, as long as their total blood volume is adequate. However, some patients, such as those with coronary artery disease, may develop severe symptoms, such as angina pectoris, at hemoglobin concentrations below about 10 g/dL. Because there are risks (e.g., transmission of viral diseases [1,2] associated with transfusion of blood, accurate monitoring of hemoglobin concentration or hematocrit facilitates both necessary transfusions and avoidance of unnecessary transfusions.

Noninvasive monitoring of fetal anemia during pregnancy is also an ideal use for the apparatuses and methods of this invention as well as measuring hematocrit and hemoglobin concentration in cord blood during pregnancy and delivery.

Additionally, continuous measurement of hemoglobin concentration using the apparatuses and methods are useful in monitoring blood volume. In this case, a known small volume of saline, $\Delta V$, is injected via i.v. and a decrease of hemoglobin concentration in blood due to the injection, $\Delta C$, is used to calculate the volume of circulating blood, V as shown in equation (1):

$$V = C \frac{\Delta V}{\Delta C} \quad (1)$$

where C represents the hemoglobin concentration in the blood.

Laser optoacoustics, is a novel technique for tissue characterization and diagnostic imaging [13–16], and the inventors have found that the technique is adaptable for hemoglobin concentration monitoring as set forth herein. Optoacoustics utilizes sensitive detection of laser-induced ultrasonic waves instead of the detection of scattered photons. An advantage of ultrasonic detection compared with optical detection is that propagation of acoustic waves in tissues is much less influenced by scattering than propagation of photon waves. Time-resolved detection of the pressure profiles by ultrasound transducers and analysis of the pressure signals allows reconstruction of optoacoustic images which resemble the distribution of optical absorption in the irradiated tissue.

In contrast to pure optical methods in which diagnostic information about tissue structure is integrated over the entire optical path, the laser optoacoustic imaging permits direct reconstruction of the absorbed energy distribution from the profile of laser-induced pressure [13–19]. The time-resolved detection and analysis of the laser-induced ultrasonic waves offers a unique possibility to visualize tissue structure at depths as great as six centimeters with spatial resolution exceeding 0.5 millimeters in optically turbid and opaque tissues [19–21] and to reconstruct optoacoustic images [22, 23].

Laser optoacoustic imaging combines the merits of optical tomography (high optical contrast) and ultrasound imaging (insignificant scattering of acoustic waves) to yield a noninvasive diagnostic modality with high contrast, sensitivity and resolution. The optoacoustic imaging in tissues is disclosed in U.S. Pat. No. 5,840,023 [24] and in U.S. application Ser. No. 09/179,791 filed Oct. 27, 1998 [25], incorporated herein by reference. The optoacoustic technique is also useful in blood oxygenation monitoring as described in U.S. application Ser. No. 09/633,597, filed Aug. 7, 2000 [26], incorporated herein by reference. Recently, optoacoustic technique was applied for noninvasive, real-time, continuous monitoring of tissue coagulation and temperature [27–29].

Theoretical Background

Although not intending to be bound by any theory, the magnitude of optoacoustic pressure is proportional to the temperature rise in the irradiated medium. The temperature rise distribution, $\Delta T(r)$, is expressed by the following equation (2):

$$\Delta T(r) = \frac{\mu_a(r)\Phi(r)}{\rho C_V} \quad (2)$$

where $\mu_a(r)$ is the absorption coefficient in the tissue, $\Phi(r)$ is the fluence distribution in the tissue, $\rho$ is the tissue density, and $C_v$ is the heat capacity at constant volume. The formula shown in equation (2) is valid upon irradiation condition of heat confinement, which means that insignificant heat diffusion occurs during laser pulse excitation.

If a short laser pulse irradiates the tissue, the irradiation condition of temporal stress confinement in the tissue volume of interest also can be satisfied. The laser irradiation under conditions of temporal stress confinement means insignificant stress (pressure) relaxation during the laser pulse excitation [30]. In a one dimensional case, the pressure rise distribution P(z) can be expressed as shown in equation (3):

$$P(z) = (\beta c^2/C_p)\mu_a F = \Gamma(z)\mu_a F(z) = \Gamma(z)\mu_a F_0 e^{-\mu_a z} \quad (3)$$

where z is tissue depth in the z direction, $\Gamma(z)$ is the efficiency of thermo-acoustic excitation often called the Grüneisen coefficient. The Grüneisen coefficient is a function of three physical parameters of the irradiated sample: the thermal expansion coefficient, $\beta$, the speed of sound, $c_s$, and the heat capacity at constant pressure, $C_p$ as given by equation (4):

$$\Gamma = \frac{\beta c_s^2}{C_p} \quad (4)$$

Irradiation conditions of temporal pressure confinement can usually be achieved by irradiating the sample with laser pulses having a pulse width having a nanosecond duration. The exponential factor $\exp(-\mu_a z)$ represents the exponential attenuation of the optical radiation in the medium due to absorption. According to equation (3) optoacoustic pressure is proportional to the Grüneisen parameter, fluence, and absorption coefficient of the medium. Equation (3) is valid for blood when the blood is irradiated with laser light in the visible and near-infrared spectra because the absorption coefficient of blood is greater than or close to the reduced scattering coefficient, $\mu'_s = \mu_s(1-g)$, where $\mu_s$ is the scattering coefficient and g is the anisotropy factor [31]. The apparatus and methods of this invention are based on the fact that the absorption coefficient of blood is proportional to hemoglobin concentration. Therefore, both the amplitude and slope of the generated optoacoustic pressure induced in blood are dependent on hemoglobin concentration.

Since z and t are related by the simple equation:

$$z=c_s t \quad (5)$$

and the spatial distribution of laser-induced pressure P(z) is detected by an acoustic transducer as its corresponding temporal profile P(t) as shown in equation (6):

$$P(t)=\Gamma \mu_a F_0 e^{-\mu_0 c_s t} \quad (6)$$

Therefore, by recording and analyzing the temporal profile of optoacoustic pressure induced in blood, one can measure the absolute value of hemoglobin concentration with high accuracy. The high z-axial resolution of the optoacoustic technique permits direct measurement of hemoglobin concentration in blood vessels, because the signal from the blood arrives at the acoustic transducer at the time defined by equation (5).

Tissues are strongly scattering media. Three major optical parameters are responsible for the distribution of light in tissues: absorption, scattering, and the tissues effective attenuation, $\mu_{eff}$, coefficients. The effective attenuation coefficient is related to $\mu_a$ and $\mu_s$ as shown in equation (7):

$$\mu_{eff}=(\mu_a(\mu_a+\mu_s(1-g)))^{1/2} \quad (7)$$

and characterizes light penetration in tissue [31]. Light penetration depth is defined as $1/\mu_{eff}$. Absorption and scattering coefficients of tissues are low in the near-infrared spectral range (from about 600 to about 1300 nm) resulting in deeper penetration of near-infrared radiation compared with light in other parts of the electromagnetic spectrum. Near-infrared radiation is the preferred spectral range for the apparatuses and methods of this invention because near-infrared light allows sufficient light penetration into a tissue for effective optoacoustic monitoring of hemoglobin concentration within the tissue including a blood vessel.

Another feature of near-infrared light as the excitation radiation is that near-infrared light induces insignificant temperature and pressure rises in the tissue being monitored resulting in little and probably no thermal or mechanical damage to the irradiated tissue.

The signal process apparatus of the present invention can comprise any analog or digital processing unit or computer capable of converting a signal into an output. Such devices include, without limitation, any digital processing unit comprising a processing unit, memory, peripherals, an operating systems and communication hardware and software. Illustrative examples include personal computers, mini-mainframe computers, or the like.

Sites and Spectral Ranges for Monitoring Hemoglobin Concentration and Hematocrit The present invention is ideally suited for measuring hemoglobin (Hb) concentrations and hematocrit in oxygenated blood or tissues having oxygenated blood. Oxygenated blood and especially highly oxygenated blood is ideal for optoacoustic monitoring because the optical properties of blood are dependent on hemoglobin concentration and oxygen saturation.

Since arterial blood is 95 to 98% oxygenated, the use of the optoacoustic signals induced in arterial blood provides highly accurate hemoglobin concentration measurements. The most preferable arteries include, but are not limited to, the aorta, radial, carotid, and femoral arteries.

Hb concentration measurements in blood or tissue can be performed with high accuracy at any wavelength within the visible and near infrared spectral range. Monitoring of hemoglobin concentration in the aorta can be performed by using a small optoacoustic probe inserted in the esophagus.

The aorta is the largest artery having a diameter between about 20 and about 25 mm and located in close proximity to the esophagus. Part of the aorta (approximately one to two inches) is in direct contact with esophagus wall. The thickness of aorta and esophagus is about 1 and 2–3 mm, respectively. This means that blood circulating in aorta represents a large optoacoustic source closely located to the optoacoustic probe, if the latter is inserted in the esophagus adjacent the part of the aorta in direct contact with the esophagus wall. The large diameter of the aorta and the short distance between the inner wall of the esophagus and blood circulating in the aorta allows substantially precise measurements of hemoglobin concentration to be obtained using the apparatuses and methods of this invention.

Detection of optoacoustic signals induced in the radial, carotid, and femoral arteries also provides a highly accurate measurement of Hb in the blood circulating through these arteries. In this case, the optoacoustic probe can be larger and can be placed on the skin surface simplifying design and use of the probe. Moreover, these latter probes can be applied to a wider patient population.

The inventors have also found that optoacoustic signals induced in veins can be used to monitor hemoglobin concentration in deoxygenated blood provided the wavelengths at isobestic points (e.g., 548, 568, 587, and 805 nm) are applied. At these wavelengths oxy- and deoxyhemoglobin have equal absorption coefficients providing accurate measurements of hemoglobin concentration even at variation of oxygen saturation in venous blood. High accuracy can also be obtained in the spectral ranges from about 400 to about 640 nm and above about 1120 nm because absorption coefficients of oxy- and deoxygenated blood are close to each other. Suitable lasers for measuring hemoglobin concentrations in veins, include, without limitation, the second harmonic of a Nd:YAG laser (532 nm), a Ti:Sapphire, dye laser, an Alexandrite laser, a ruby laser, an optical parametric generator, or any other source of short optical pulses in these spectral ranges.

The inventors have found that attenuation of light with a wavelength above about 1300 to about 1350 nm in blood is dependent mostly on hematocrit, but not on hemoglobin concentration. Optoacoustic signal characteristics in this spectral range will be sensitive to the changes in blood scattering and therefore, to changes in hematocrit. Measurement of hematocrit is especially important when hematocrit does not follow hemoglobin concentration (e.g., during blood transfusions, etc.).

Design of Optoacoustic Probes

The inventors have found that a preferred optoacoustic monitoring system of this invention includes an optoacoustic probe that will provide both irradiation of blood and detection of optoacoustic waves by an acoustic transducer. Such optoacoustic probe include a light delivery system (usually fiber-optic system) and a sensitive piezoelectric element to detect the optoacoustic waves. Different configurations of the probes are possible, depending on the site of monitoring and depth of the blood vessels. The optoacoustic probe can be placed on the skin surface, when monitoring blood in radial, femoral, carotid or other arteries or veins located relatively close to the skin surface, where relatively close means less than about 5 cm from the skin surface and preferably about 2 cm from the skin surface.

For hemoglobin monitoring in the aorta due to limitation in space in the esophagus, small needle hydrophones are incorporated into optoacoustic probes to minimize the dimensions of the probe. The thickness of the needle hydrophones is generally about 1 mm which are incorporated into small optoacoustic probes with the transverse dimensions of about 2 to about 3 mm. The length of such optoacoustic probe is generally from about 1 to about 2 meters or more to provide delivery of light and signal recording by a distant optoacoustic system.

The optoacoustic probes of this invention can have an acoustic transducer(s) surrounded by optical fiber(s) or vice versa. Moreover, the optical fiber(s) and the acoustic transducer(s) can be arranged in an adjacent configuration or can be housed in two different probes, an excitation probe and an receiving probe.

EXPERIMENTAL RESULTS

The inventors performed experiments with blood in vitro and in phantoms to test the capability of the optoacoustic technique to monitor hemoglobin concentration. Heparinized sheep arterial blood in a plastic cuvette was irradiated by nanosecond Nd:YAG laser pulses (wavelength=1064 nm). The blood was under a layer of mineral oil to avoid contact with air. Ultrasonic gel was used to provide acoustic contact between the acoustic transducer and the cuvette. Pulsed laser irradiation of blood and detection of optoacoustic waves were performed from two opposite surfaces of the cuvette. Optoacoustic pressure waves induced in blood propagated to the transducer and were recorded by a scope. The initial volume of whole blood with a hemoglobin concentration of 12.4 g/dL was 30 mL. Blood dilutions were performed with 1-mL saline injections into the blood sample with a syringe. The influence on optoacoustic pressure signals due to the change in blood volume is displayed in FIG. 1 for four (4) different volumes. As shown in FIG. 1, saline injections dramatically changed the amplitude and slope of the pressure signal.

Figure 2:
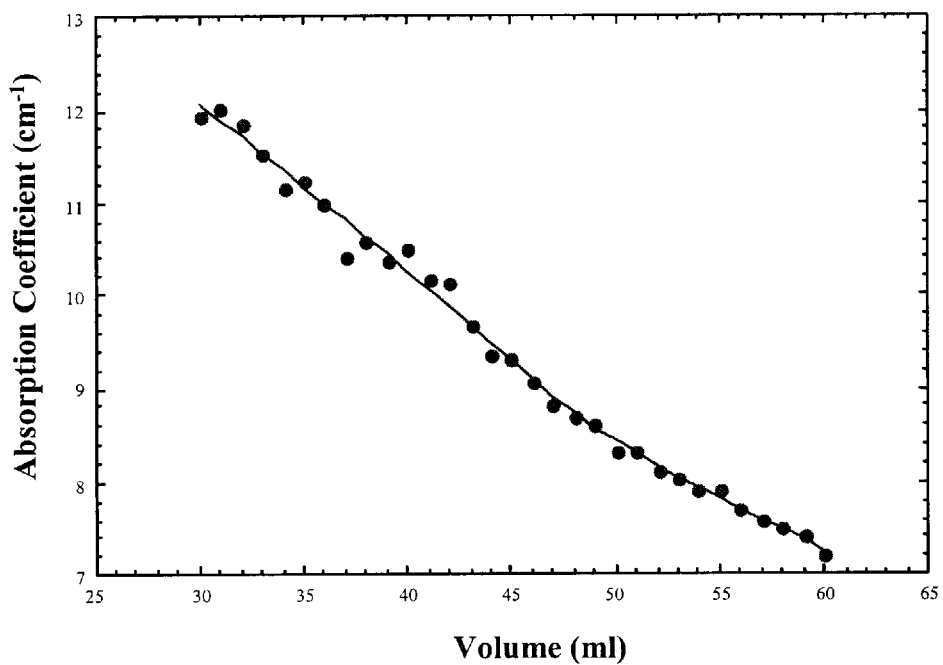
FIG. 2 depicts a graph of blood absorption coefficient calculated from optoacoustic slopes at different volumes.
Figure 3:
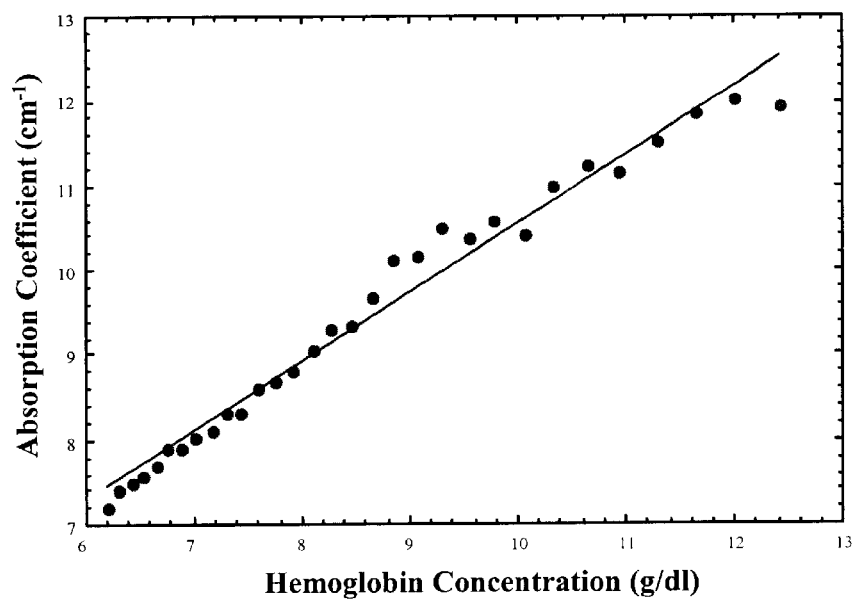
FIG. 3 depicts a graph of blood absorption coefficient calculated from optoacoustic slopes at different hemoglobin concentrations.

Blood absorption coefficient calculated from the pressure slopes decreased with increasing blood volume as shown in FIG. 2 due to blood dilution. Since the initial blood volume and volume of injected saline are known, one can calculate a hemoglobin concentration in blood after each saline injection. The optoacoustic signal slope was found to be linearly dependent on hemoglobin concentration as shown in FIG. 3.

Figure 4:
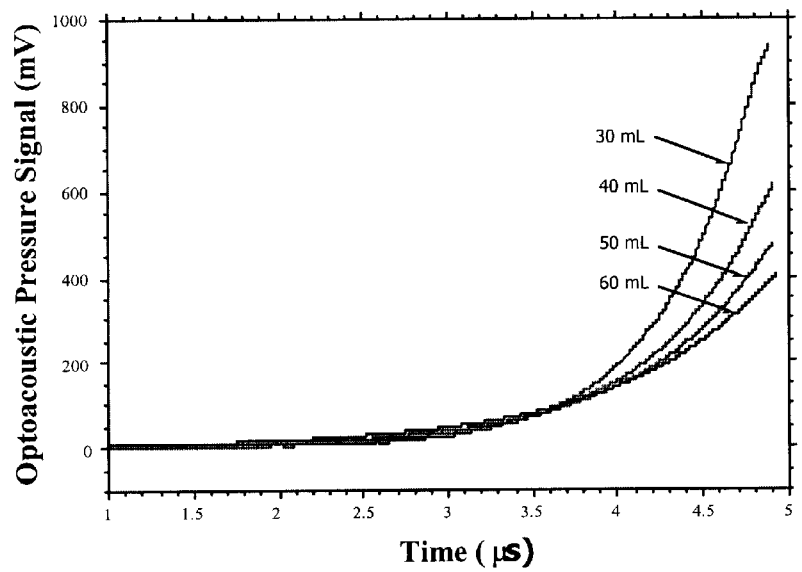
FIG. 4 depicts a graph of optoacoustic signals induced in blood irradiated through 1-cm turbid gelatin slab at different volumes.
Figure 5:
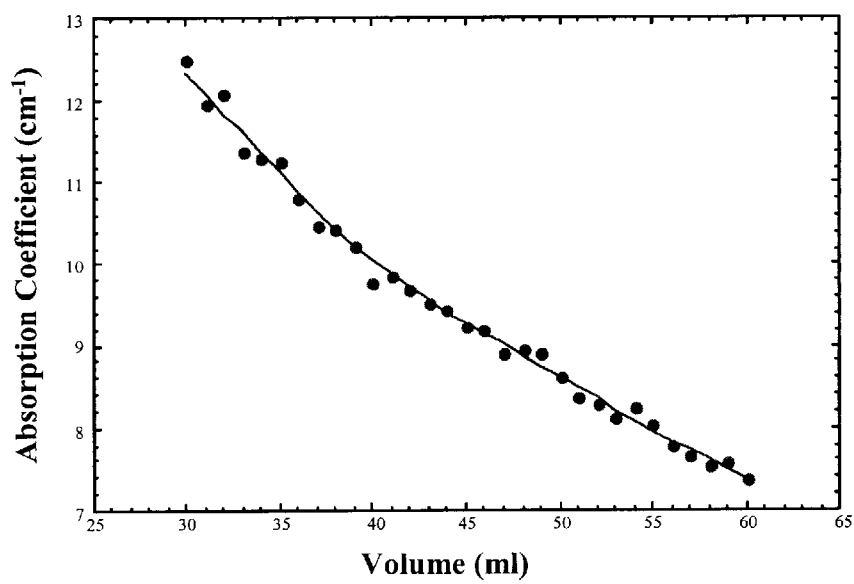
FIG. 5 depicts a graph of blood absorption coefficient calculated from optoacoustic slopes at different blood volumes where the blood was irradiated through 1-cm turbid gelatin slab.
Figure 6:
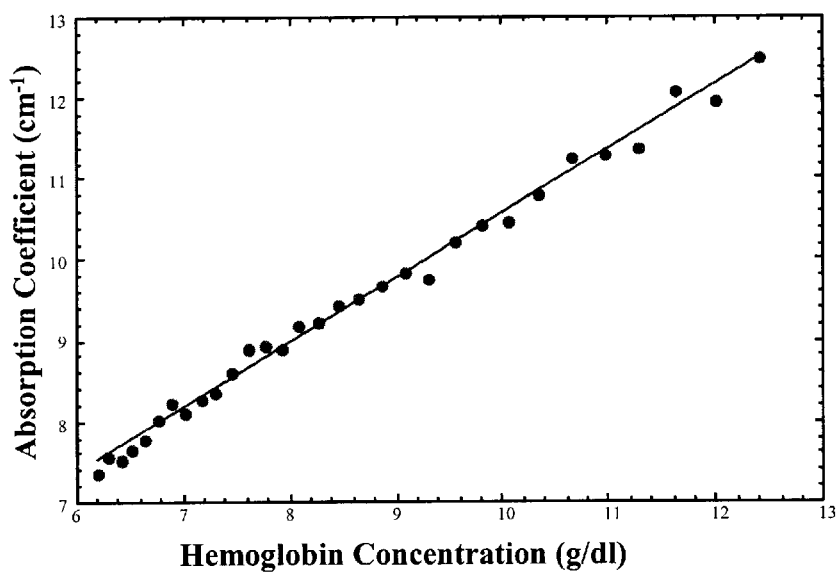
FIG. 6 depicts a graph of blood absorption coefficient calculated from the optoacoustic slopes as a function of hemoglobin concentration where the blood was irradiated through 1-cm turbid gelatin slab.

Similar experiments and calculations were performed when blood was irradiated through a turbid gelatin slab with the thickness of 1 cm. The gelatin slab had optical properties similar to that of tissues in the near infrared spectral range ($\mu_a$=0.6 cm$^{-1}$ and $\mu_s'$=2.9 cm$^{-1}$) and can be used to simulate a tissue layer in vivo. The results presented in FIGS. 4, 5, and 6 indicate that the addition of the turbid slab did not decrease the accuracy of the blood Hb concentration measurements. The amplitude of the signals is close to that recorded from blood irradiated without the gelatin slab despite attenuation, because scattering in the slab resulted in an increase of irradiated blood area and, therefore, an increase in optoacoustic signal amplitude.

Figure 7:
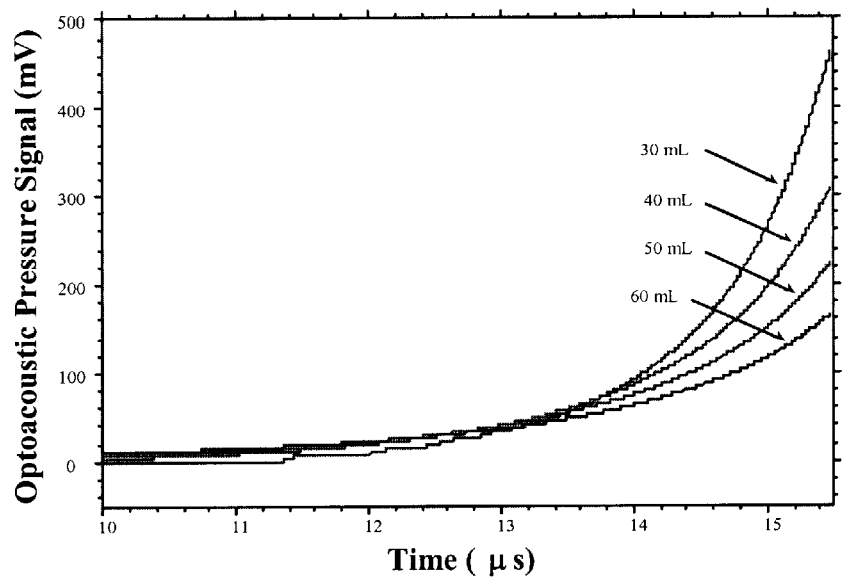
FIG. 7 depicts a graph of optoacoustic signals induced in naphthol green solution irradiated through 1-cm turbid gelatin slab at different volume.
Figure 8:
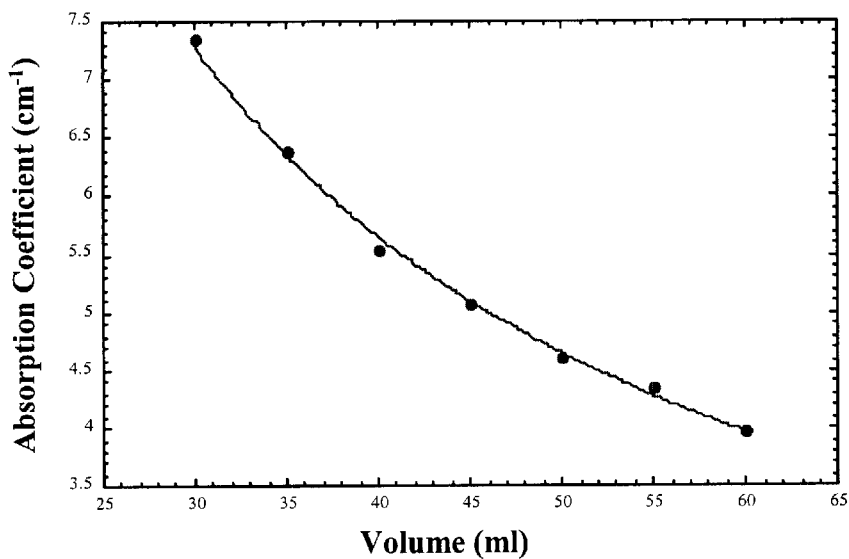
FIG. 8 depicts a graph of absorption coefficient of naphthol green solution calculated from the optoacoustic slopes at different volume. The solution was irradiated through 1-cm turbid gelatin slab.

Experiments were also performed with an aqueous solution colored with an absorbing dye (naphthol green) simulating blood. The experiment demonstrated similar results to the previous experiments as shown in FIGS. 7, 8, 9.

To monitor hemoglobin concentration and hematocrit in vivo, irradiation of tissue by laser light and detection of the laser-induced optoacoustic waves should generally be performed A from the same side of the tissue. The inventors designed, built, and, tested different optoacoustic probes: (1) with a ring shape piezoelectric element and optical fiber in the center of the ring (see FIG. 10A); (2) with optical fibers surrounding a disc shaped piezoelectric element (see FIG. 10B); and (3) with optical fibers adjacent to a disc shaped piezoelectric element (see FIG. 10C). Each of these configurations has advantages and each used a PVDF based transducer. The most preferable probe configuration for hemoglobin monitoring includes a ring shaped piezoelectric element with optical fibers in the center of the ring as shown in FIG. 10A. The results of tests of the probe of FIG. 10A are presented below. Looking at FIGS. 10A–C, a probe generally 100 is shown to include a housing 102 which can be composed of metal or other structural material such as plastic, an optical system 104, a backing element 106, a piezoelectric element 108 and an isolating layer 110. The optical system 104 includes an optical fiber 112, an optical screen 114 and an acoustic screen 116. The system 104 would connect at its proximal end to a pulsed light source such as a laser (not shown), while its distal end 118 terminates flush with the housing 102 at the probe's distal end 120. The probe of FIG. 10A has the optical system 104 passing through a center 122 of a ring-shaped piezoelectric element 108. The probe of FIG. 10B has the optical system 104 distributed around a disk shaped piezoelectric element 108. And, the probe of FIG. 10C has the optical system 104 positions next to (a side-by-side arrangement) the piezoelectric element 108 which can be of any desired shape.

Referring now to FIG. 10D and E, two preferred embodiments of esophagus probes 200 is shown to includes a housing 202 which can be composed of metal or other structural material such as plastic, an optical system 204, a backing element 206, a piezoelectric element 208 and an isolating layer 210. The optical system 204 includes an optical fiber 212, an optical screen 214 and an acoustic-screen 216. The system 204 would connect at its proximal end to a pulsed light source such as a laser (not shown), while its distal end 218 terminates flush with the housing 202 at the probe's distal end or tip 220. The probe of FIG. 10D has the optical system 204 passing through a center 222 of a ring-shaped piezoelectric element 208. The probe of FIG. 10B also has the optical system 204 passing through the center 220 of a ring-shaped piezoelectric element 208, but the distal end 218 of the optical system 204, the transducer 208 and the isolating layer 210 so that the tip 220 is oriented at a right angle to the main body 224 of the probe 200. Of course, the tip 220 can be oriented at any angle relative to the main body 224 provided that the tip 220 can contact the esophagus wall adjacent the aorta.

Results Obtained with the Optoacoustic Probe of FIG. 10A

Figure 11:
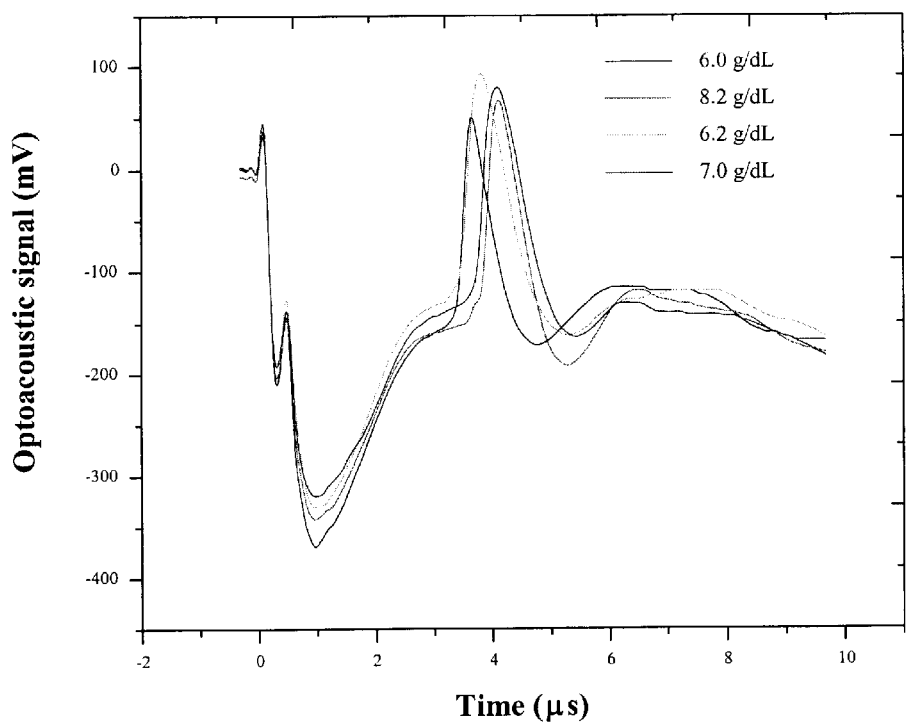
FIG. 11 depicts a graph of optoacoustic signals from aorta phantom with blood at different Hb concentrations.
Figure 12:
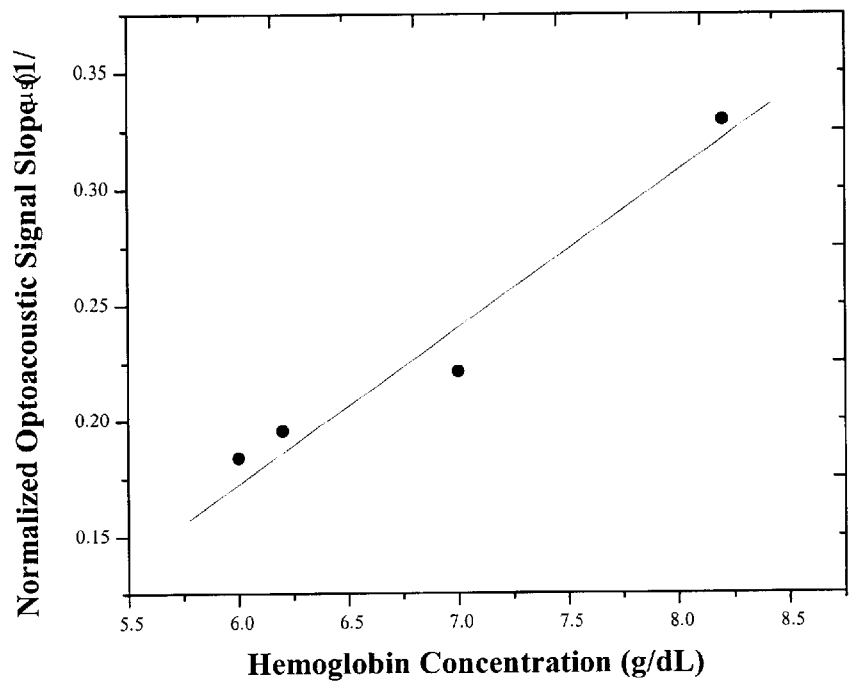
FIG. 12 depicts a graph of slope of optoacoustic signal recorded from aorta phantom as a function of Hb concentration.

The inventors performed experiments with whole sheep blood and absorbing solutions in phantoms simulating aorta and radial artery. Rubber tubes having a diameter of about 25 mm and a length of about 50 mm were filled with blood with different Hb concentrations (6.0, 6.2, 7.0, and 8.0 g/dL). The tubes were then covered with a 3-mm turbid gelatin slab to provide irradiation and detection conditions similar to ones for optoacoustic monitoring of hemoglobin concentration in aorta. The optoacoustic signals induced in blood start at about 3 to about 3.5 $\mu$s depending on hemoglobin concentration as shown in FIG. 11. Looking at FIG. 11, the first two sharp peaks are signals induced in the thin metal housing of the probe. The flexible tubes and gelatin slabs used to simulate a real aorta and esophagus wall with different thicknesses resulted in a shift in time for the signals induced in the blood within the tubes. Despite differences in irradiation and detection conditions for the tubes, the optoacoustic slope calculated from the recorded signals increased linearly with Hb concentration as shown graphically in FIG. 12. The signals were normalized before the slope calculations. Calculation of the normalized signal slope provides measurement of Hb concentration with high accuracy, e.g. about 0.5 g/dL.

Figure 13:
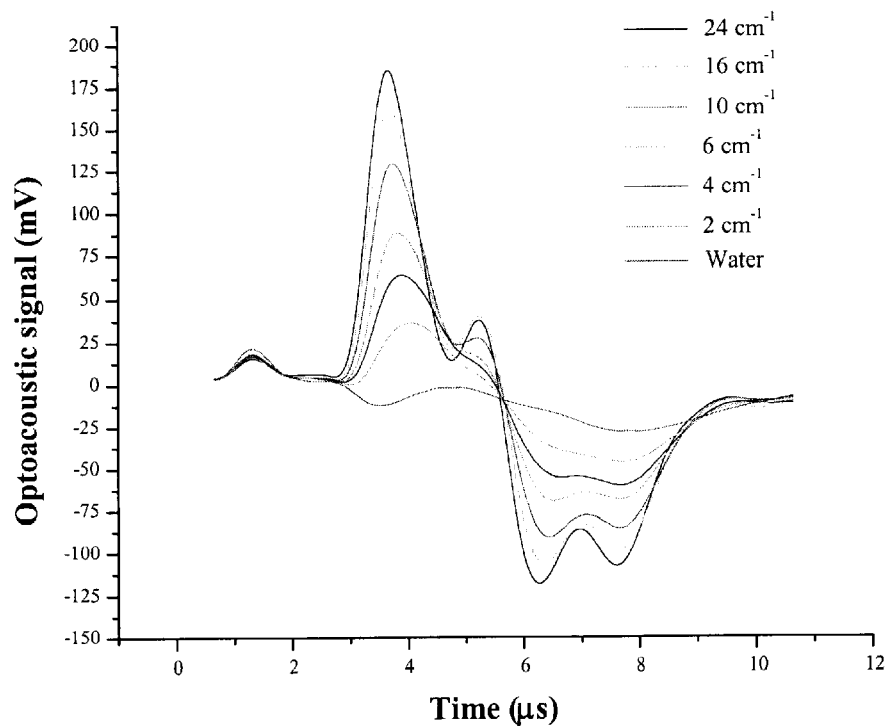
FIG. 13 depicts a graph of optoacoustic signals recorded from 2.2-mm tube with solution at different absorption coefficient.
Figure 14:
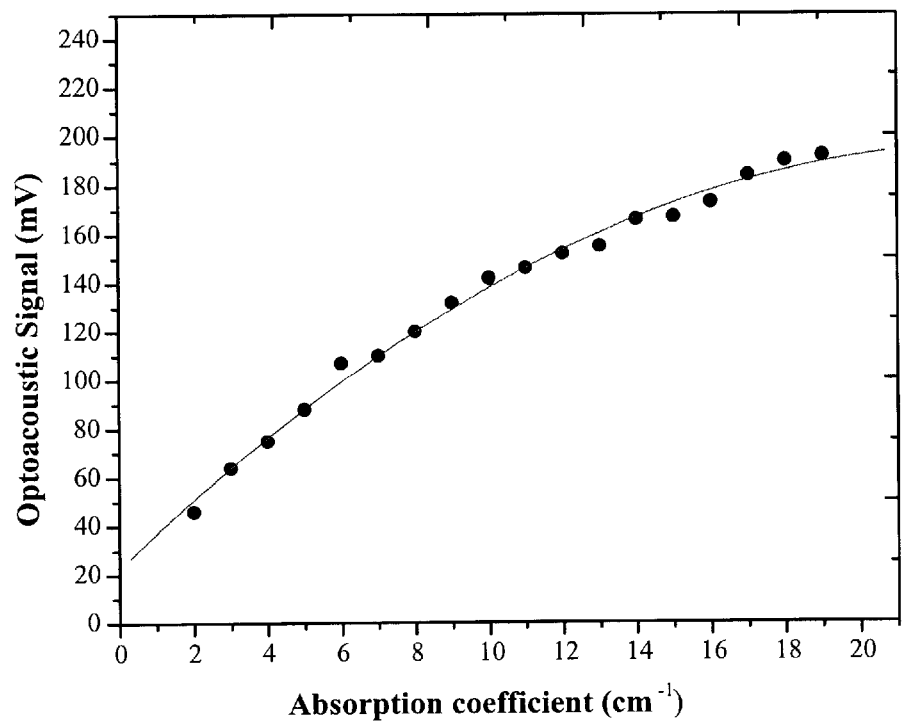
FIG. 14 depicts a graph of amplitude of optoacoustic signal recorded from the 2.2-mm tube as a function of Hb concentration.
Figure 15:
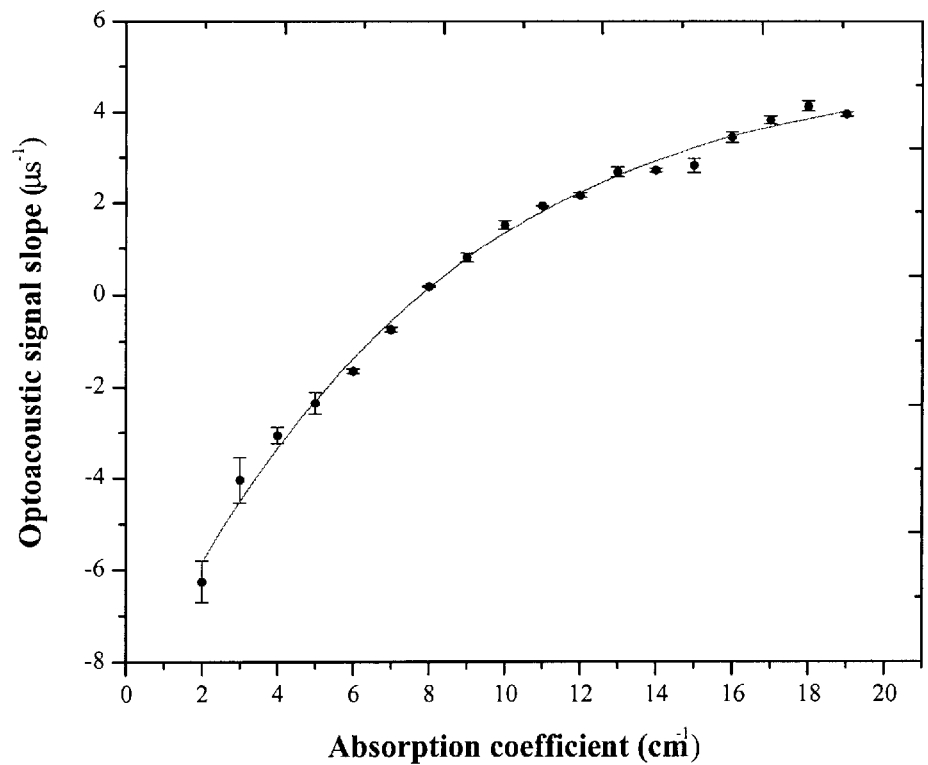
FIG. 15 depicts a graph of slope of optoacoustic signal recorded from the 2.2-mm tube as a function of Hb concentration.

Referring now to FIG. 13, optoacoustic signals recorded from a phantom (2.2-mm plastic tube in a turbid solution) simulating radial artery are shown. The absorbing solution in the tube had an absorption coefficient of about 2 to about 24 $cm^{-1}$. The first peak at about 1.2 μs is a signal induced in the housing of the probe and the turbid solution. The signals induced in the tube start at about 3 μs representing time of flight of the optoacoustic waves from the upper surface of the tube to the probe. Both amplitude and temporal profile of the signals induced in the tube are dependent on the solution absorption coefficient. The optoacoustic signal amplitude increases gradually with absorption coefficient as shown in FIG. 14. The signal from the solutions with high absorption coefficient values has two positive peaks, while only one positive peak is recorded from solutions with low absorption coefficient values. The optoacoustic signals were normalized and their first derivatives (slope) were calculated. The slope of the signals at about 5 μs is the most sensitive to changes in the absorption coefficient as shown in FIG. 15. It is positive for solutions with high absorptions and negative for ones with low absorptions. The measurement and calculation of the slope can be used to provide accurate measurement of blood Hb concentrations.

Figure 16:
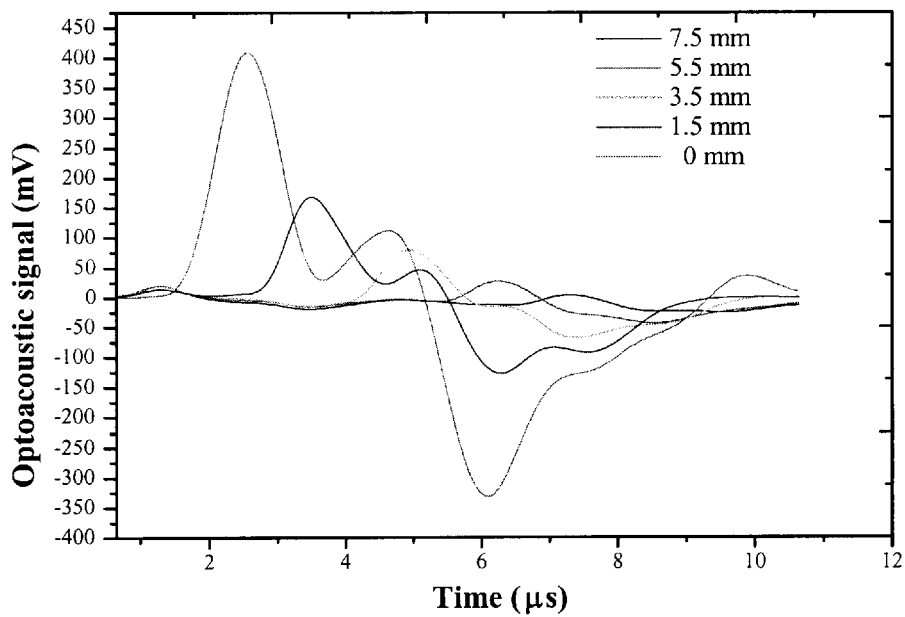
FIG. 16 depicts a graph of optoacoustic signal recorded from the tube at different axial distance between the tube and the probe.
Figure 17:
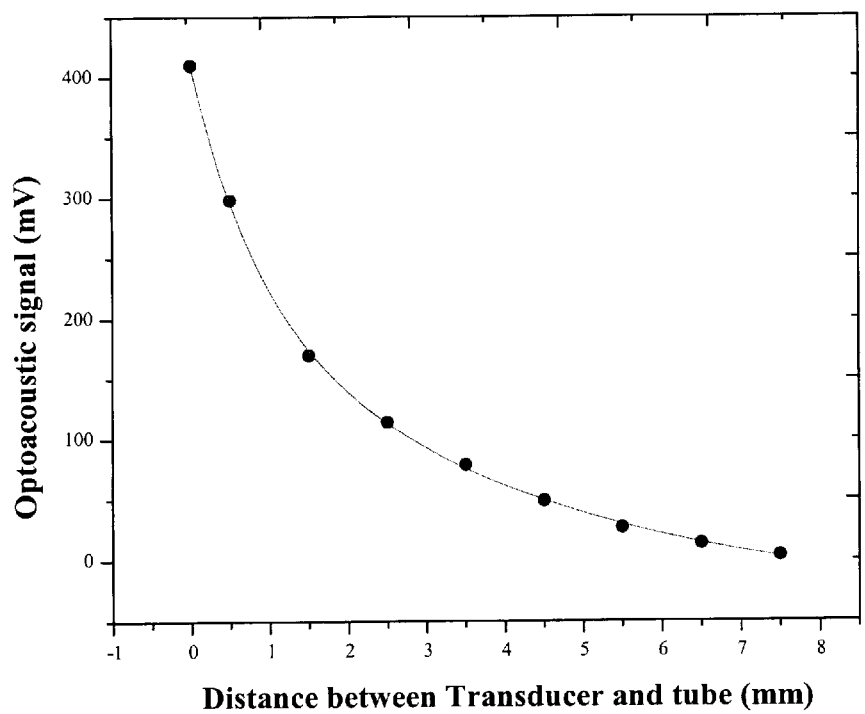
FIG. 17 depicts a graph of amplitude of optoacoustic signal recorded from the tube as a function axial distance between the tube and the probe.
Figure 18:
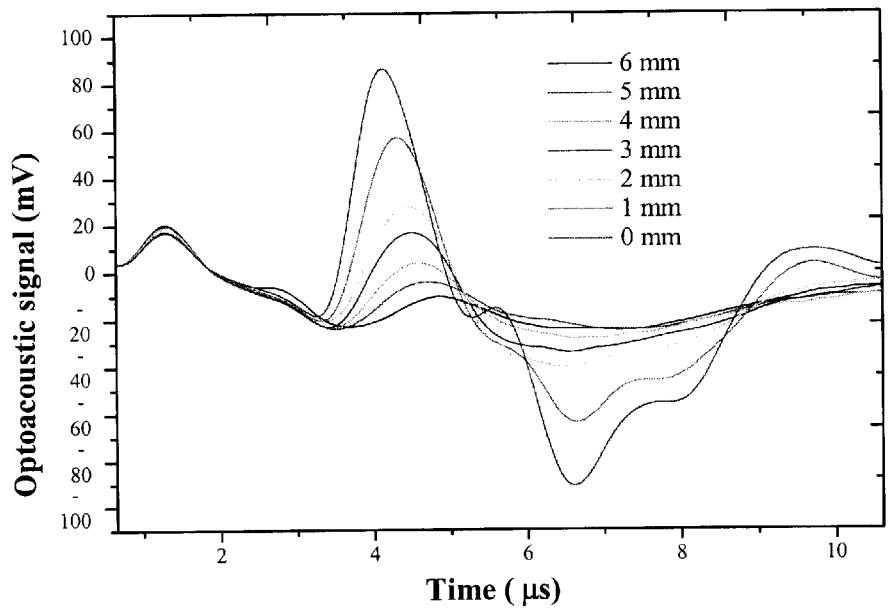
FIG. 18 depicts a graph of optoacoustic signal recorded from the tube at different lateral distance between the tube and the probe.
Figure 19:
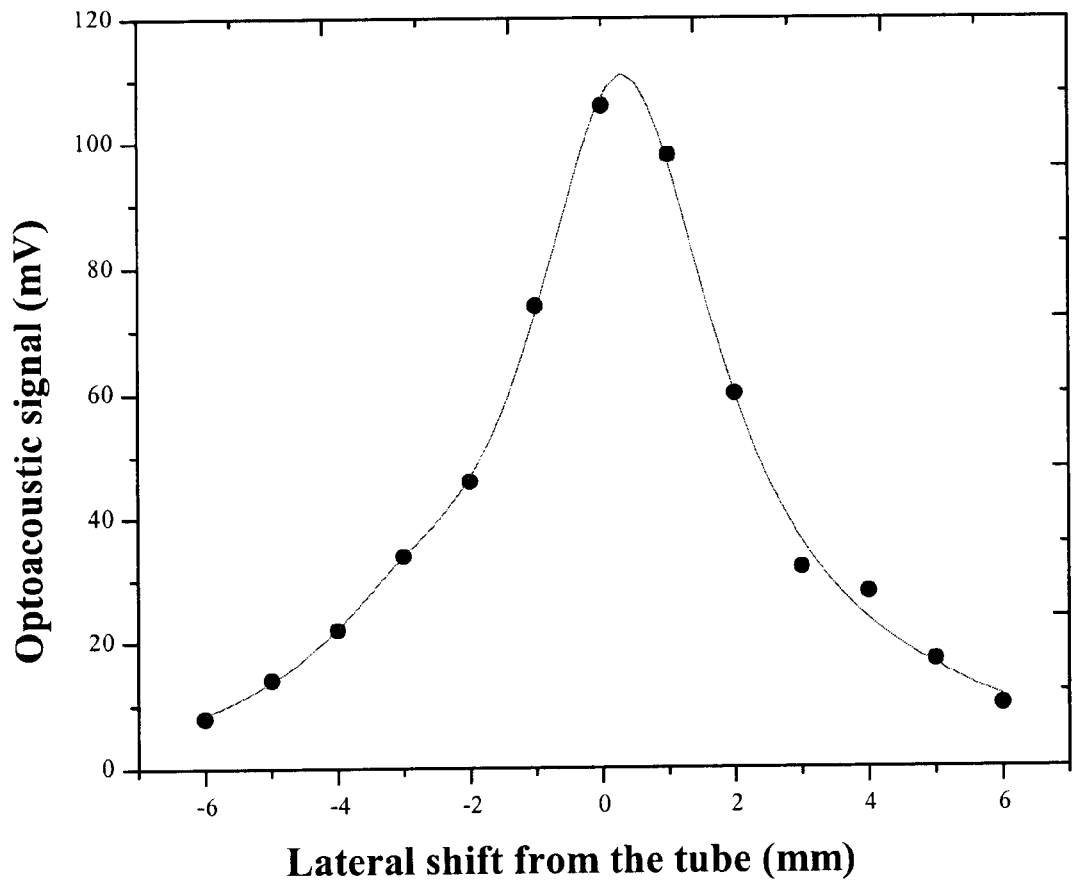
FIG. 19 depicts a graph of amplitude of optoacoustic signal recorded from the tube as a function of lateral displacement of the probe with respect to the tube.

Referring now to FIG. 16, the optoacoustic signals recorded at different axial distance between the tube and the probe for solution with an absorption coefficient of about 13 $cm^1$ are shown. The variation of the distance simulated different thicknesses of tissue between the probe and a simulated artery (radial, carotid, or femoral). The position of the signal changes with the distance indicating the depth of the artery in the solution, i.e., its location in a tissue. The temporal profile of the signals change slightly with depth while the signal amplitude sharply decreases with increasing depth due to stronger attenuation of light and propagation of the optoacoustic signals from the cylindrical source as shown in FIG. 17. Lateral displacement of the probe with respect to the tube changes both amplitude and profile of the signals as shown in FIGS. 18 and 19. These data indicate that lateral alignment of the probe is important for accurate measurement of Hb concentration. Thus, by laterally scanning the optoacoustic probe on the skin surface, the practitioner can obtain highly accurate Hb concentration measurements, where the scanning is used to maximize the measuring process—maximize signal amplitude.

REFERENCES

1. Goodnough L T. Brecher M E. Kanter M H. AuBuchon J P. Transfusion medicine. Second of two parts—blood conservation. *New England Journal of Medicine.* 340(7):525–33, 1999.
2. Goodnough L T. Brecher M E. Kanter M H. AuBuchon J P. Transfusion medicine. First of two parts—blood transfusion. *New England Journal of Medicine.* 340(6):438–47, 1999.
3. Silver M J. Li Y H. Gragg L A. Jubran F. Stoller J K. Reduction of blood loss from diagnostic sampling in critically ill patients using a blood-conserving arterial line system. *Chest.* 104(6):1711–5, 1993.
4. Zimmerman J E. Seneff M G. Sun X. Wagner D P. Knaus W A. Evaluating laboratory usage in the intensive care unit: patient and institutional characteristics that influence frequency of blood sampling. *Critical Care Medicine.* 25(5):737–48, 1997.
5. Henry M L. Garner W L. Fabri P J. Iatrogenic anemia. *American Journal of Surgery.* 151(3):362–3, 1986.
6. Foulke G E. Harlow D J. Effective measures for reducing blood loss from diagnostic laboratory tests in intensive care unit patients. *Critical Care Medicine.* 17(11):1143–5, 1989.
7. Smoller B R. Kruskall M S. Phlebotomy for diagnostic laboratory tests in adults. Pattern of use and effect on transfusion requirements. *New England Journal of Medicine.* 314(19):1233–5, 1986.
8. Tanaka Y. Morimoto T. Watari H. Miyazaki M. Continuous monitoring of circulating blood hematocrit. *Japanese Journal of Physiology.* 26(4):345–53, 1976.
9. Kaiwa T. Mori T. Kijima T. Nogawa M. Nojiri C. Takatani S. Measurement of blood hematocrit inside the magnetically suspended centrifugal pump using an optical technique: application to assessment of pump flow. *Artificial Organs.* 23(6):490–5, 1999.
10. Jabara A E. Mehta R L. Determination of fluid shifts during chronic hemodialysis using bioimpedance spectroscopy and an in-line hematocrit monitor. *ASAIO Journal.* 41(3):M682–7, 1995.
11. Ronco C, Brendolan A, and Bellomo R. Online monitoring in continuous renal replacement therapies. *Kidney International.* 36, *Suppl.* 72; S-8–S-14, 1999.
12. Maasrani M. Jaffrin M Y. Boudailliez B. Continuous measurements by impedance of haematocrit and plasma volume variations during dialysis. *Medical & Biological Engineering & Computing.* 35(3):167–71, 1997.
13. Esenaliev R. O., Oraevsky A. A., Letokhov V. S., Karabutov A. A., Malinsky T. V. Studies of Acoustical and Shock Waves in the Pulsed Laser Ablation of Biotissue. *Lasers Surg. Med.,* 1993, v.13, pp.470–484.
14. Oraevsky A. A., Jacques S. L., Esenaliev R. O., Tittel F. K. Imaging in layered tissues using time-resolved detection of laser-induced stress transients. *SPIE Proc.* 1994, v. 2134, pp. 122–128.
15. Oraevsky A. A., Esenaliev R. O., Jacques S. L., Tittel F. K. Laser opto-acoustic tomography for medical diagnostics: principles. *SPIE Proc.* 1996, v. 2676, pp. 22–31.
16. Esenaliev R. O., Oraevsky A. A., Jacques S. L., Tittel F. K. Laser opto-acoustic tomography for medical diagnostics: Experiments with biological tissues. *SPIE Proc.* 1996, v. 2676, pp. 84–90.
17. Oraevsky A. A., Esenaliev R. O., Jacques S. L., Tittel F. K. Laser Optoacoustic tomography for breast cancer diagnostics, In: "Trends in Optics and Photonics", vol. 11, ed. by R R Alfano and J G Fujimoto, OSA Publishing House, pp. 316–321 (1996).
18. Oraevsky A. A., Esenaliev R. O., Karabutov A. A. Optoacoustic Imaging in Layered Tissues: Signal Processing. *SPIE Proc.* 1997, v. 2979, pp. 59–70.
19. Esenaliev R. O., Karabutov A. A., Tittel F. K., Fornage B. D., Thomsen S. L., Stelling C., Oraevsky A. A. Laser Optoacoustic Imaging for Breast Cancer Diagnostics: Limit of Detection and Comparison with X-ray and Ultrasound Imaging. *SPIE Proc.* 1997, v. 2979, pp. 71–82.
20. Esenaliev R. O., Alma H., Tittel F. K., Oraevsky A. A. Axial resolution of laser optoacoustic imaging: Influence of acoustic attenuation and diffraction. *SPIE Proc.* 1998, v. 3254, pp. 294–301.
21. Esenaliev R O, Karabutov A A, Oraevsky A A. Sensitivity of Laser Opto-Acoustic Imaging for Detection of Early Breast Cancer. Journal of Quantum Electronics, v.5(4), 1999, pp. 981–988.

22. Oraevsky A. A., Andreev V. G., Karabutov A. A., and Esenaliev R. O. Two-Dimensional Opto-Acoustic Tomography Transducer Arrey and Image Reconstruction Algorithm. *SPIE Proc.* 3601:256–267, 1999.
23. Oraevsky A. A, Andreev V. G., Karabutov A. A., Fleming D. R., Gatalica Z., Singh H., and Esenaliev R. O. Laser Opto-Acoustic Imaging of the Breast: Detection of Cancer Angiogenesis. *SPIE Proc.* 3597, 1999, pp. 256–267.
24. A. A. Oraevsky, S. L. Jacques, R. O. Esenaliev, "Optoacoustic Imaging for Medical Diagnostics", U.S. Pat. No. 5,840,023.
25. Esenaliev R. O., Oraevsky A. A., Motamedi M., Karabutov A. A. "Real-time Optoacoustic Monitoring of Changes in Tissue Properties" U.S. patent application Ser. No. 09/179,791 filed Oct. 27, 1998.
26. Esenaliev R. O., Motamedi M., Prough D. S. Oraevsky A. A. "Optoacoustic Monitoring of Blood Oxygenation" U.S. patent application Ser. No. 09/633,597, filed Aug. 7, 2000.
27. Esenaliev R. O., Larin K. V., Larina I. V., Motamedi M., Oraevsky A. A. Optical properties of normal and coagulated tissues: Measurements using combination of optoacoustic and diffuse reflectance techniques. *SPIE Proc.* 1998, v. 3726, pp. 560–566.
28. Esenaliev R. O., Larina I. V., Larin K. V, Motamedi M, Karabutov A A, Oraevsky A A. Laser Optoacoustic Technique for Real-Time Measurement of Thermal Damage in Tissues. *SPIE Proc.* 3594, 1999, pp.101–113.
29. Esenaliev R. O., Oraevsky A. A., Larin K. V., Larina I. V., Motamedi M. Real-Time Optoacoustic Monitoring of Temperature in Tissues. *SPIE Proc.* 3601:268–275, 1999.
30. Gusev V. E., Karabutov A. A. "Laser Optoacoustics", *AIP Press, New York*, 1993.
31. Welch A J, Van Gemert M J C, Optical-thermal response of laser-irradiated tissue, *New York. Plenum Press*, 1995.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A system for measuring hemoglobin concentrations and hematocrit comprising:
    a pulsed optical source adapted to generate short optical pulses to provide irradiation of a blood vessel or tissue site;
    an optical delivery system adapted to deliver the optical pulses to the blood vessel or tissue site, where the optical deliver system includes a proximal end in light communication with the source and a distal end out of which the optical pulses exit;
    an adjustable probe including a housing, an acoustic transducer adapted to detect pressure waves resulting from the optical pulses impinging on the blood vessel or tissue site and mounted near a distal end of the probe, where the transducer has sufficient sensitivity, temporal resolution, and bandwidth to collect data from which a hemoglobin concentration can be derived and a cable connected to the transducer, where the probe is adapted to receive the distal end of the optical delivery system at its proximal end and situate the distal end of the optical delivery system flush with the housing at the distal end of the probe to provide appropriate irradiation conditions and acoustic contact between the blood vessel or tissue site and the acoustic transducer; and
    an electronic signal recording and processing system connected to the cable where the signal recording and processing system includes a digital processing unit or computer calculating a hemoglobin concentration from the recorded optoacoustic pressure profiles and amplitudes.

2. The system of claim 1, wherein the source produces tight optical pulses in the spectral range from about 400 to about 2500 nm.

3. The system of claim 1, wherein the source comprises at least two sources having producing optical pulses of different wavelengths.

4. The system of claim 1, wherein the source comprises a laser.

5. The system of claim 1, wherein the vessel comprises an aorta and wherein the probe inserted into an esophagus and the irradiation occurs through the esophagus wall adjacent the arota.

6. The system of claim 1, wherein the vessel comprises a radial artery.

7. The system of claim 1, wherein the vessel comprises a carotid artery.

8. The system of claim 1, wherein the vessel comprises a brachial artery.

9. The system of claim 1, wherein the vessel comprises a femoral artery.

10. The system of claim 1, wherein the vessel comprises an artery.

11. The system of claim 1, wherein the vessel comprises a vein.

12. The system of claim 1, wherein the vessel comprises a vein under the skin or in a hollow organ.

13. The system of claim 12, wherein the optical pulses have a wavelength of about 548, 568, 587, 805 nm or mixture or combinations thereof or the wavelength is in spectral ranges from about 400 to about 640 or above about 1120 nm where an absorption coefficient of oxy- and deoxygenated blood are similar so that the hemoglobin concentration can be derived from both oxygenated and deoxygenated blood.

14. The system of claim 1, wherein the source comprises a Nd:YAG laser or a tunable laser or an optical parametric generator or mixtures or combinations thereof.

15. The system of claim 14, wherein the tunable lasers comprises a Ti:Sapphire laser or a dye laser or mixtures or combinations thereof.

16. The system of claim 1, wherein the system is used for hemoglobin concentration or hematocrit measurements in the spectral range from 400 nm to 2500 nm.

17. The system of claim 1, wherein the system is used for blood volume measurements.

18. The system of claim 1, wherein the system is used for ultrasound-guided optoacoustic monitoring of fetal anemia during pregnancy.

19. The system of claim 1, wherein the system is used for measuring hematocrit and a hemoglobin concentration in cord blood.

20. The system of claim 1, wherein the system is used for hemoglobin concentration monitoring in patients with kidney failure or patients on dialysis.

21. A system for measuring hemoglobin concentrations and hematocrit comprising:
    a pulsed optical source adapted to generate short optical pulses;

an optical delivery system including a proximal end in light communication with the source and a distal end out of which the optical pulses exit, where the system is adapted to deliver the optical pulses to a blood vessel;

an adjustable probe including
- a housing including a distal end and a proximal end,
- an acoustic transducer mounted in the distal end of the housing and having sufficient sensitivity, temporal resolution, and bandwidth to collect data from which a hemoglobin concentration can be derived,
- an optical mount mounted in the distal end of the housing into which the distal end of the optical deliver system is inserted, and
- a cable connected to the transducer at its proximal end, where the transducer is adapted to detect pressure waves resulting from the optical pulses impinging on the blood vessel, where the distal end of the housing is adapted to provide appropriate irradiation and acoustic contact between the blood vessel and the optical delivery system and transducer mounted in the distal end of the housing; and an electronic signal recording and processing system including a digital processing unit, where the recording and processing system is connected to a distal end of the cable and adapted to receive and record transducer generated optoacoustic pressure profiles and amplitudes and where the digital processing unit is adapted to calculate a hemoglobin concentration from the recorded optoacoustic pressure profiles and amplitudes.

22. The system of claim 21, wherein the system is used for hemoglobin concentration or hematocrit measurements in the spectral range from 1350 nm to 2500 nm.

23. The system of claim 21, wherein the blood vessel comprises an artery or a vein.

24. The system of claim 23, wherein the artery is selected from the group consisting of the arota, a radial artery, a carotid artery, a brachial artery, a femoral artery.

25. The system of claim 21, wherein the source is a laser and produces optical pulses in the spectral range from about 400 to about 2500 nm and wherein the system is used for blood volume measurements, is used for optoacoustic monitoring of fetal anemia during pregnancy, is used for measuring hematocrit and a hemoglobin concentration in cord blood or is used for hemoglobin concentration monitoring in patients with kidney failure or patients on dialysis.

* * * * *